United States Patent [19]
Schmid

[11] Patent Number: 5,819,921
[45] Date of Patent: *Oct. 13, 1998

[54] CALCIUM HYDROXIDE PACKAGE AND METHOD OF FORMING SAME

[75] Inventor: Carl E. Schmid, Easton, Conn.

[73] Assignee: Centrix, Inc., Shelton, Conn.

[*] Notice: This patent issued on a continued prosecution application filed under 37 CFR 1.53(d), and is subject to the twenty year patent term provisions of 35 U.S.C. 154(a)(2).

[21] Appl. No.: 766,453

[22] Filed: Dec. 12, 1996

[51] Int. Cl.$^6$ .......................................... A61C 5/04
[52] U.S. Cl. .................. 206/210; 206/63.5; 206/368; 53/173
[58] Field of Search ................. 206/205, 210, 206/207, 63.5, 363–366, 368, 369, 524.1, 524.5, 438; 53/173, 449

[56] References Cited

U.S. PATENT DOCUMENTS

| | | | |
|---|---|---|---|
| 1,280,687 | 10/1918 | Dudley | 206/210 |
| 1,307,249 | 6/1919 | Franklin | 206/210 |
| 1,378,806 | 5/1921 | Ausubel | 206/210 |
| 2,558,742 | 7/1951 | Ericsson et al. | 206/210 |
| 2,812,231 | 11/1957 | Zar | 206/205 |
| 4,942,966 | 7/1990 | Kemp | 206/521 |
| 5,336,088 | 8/1994 | Discko, Jr. | |

Primary Examiner—Paul T. Sewell
Assistant Examiner—Luan K. Bui
Attorney, Agent, or Firm—Fattibene & Fattibene; Arthur T. Fattibene; Paul A. Fattibene

[57] ABSTRACT

A calcium hydroxide package and method of forming the package that includes a sealed vial containing a capsule having a connected needle forming a nozzle which is open at the discharge end. The capsule is prefilled with a predetermined amount of calcium hydroxide formulation that is confined within the capsule by an end plug that functions as a piston to extrude the calcium hydroxide formulation from the capsule and directly to the tooth when used. Disposed within the sealed vial containing the capsule, prefilled with the calcium hydroxide formulation, is a quantity of preservative liquid or distilled water saturated with calcium hydroxide to prevent dehydration or decomposition of the calcium hydroxide formulation during shipping or storage, and wherein the vial with the capsule and liquid sealed therein can be subsequently sterilized by gamma radiation to ensure sterility of the calcium hydroxide and to prevent growth in the sealed container containing distilled water. In another form of the invention, the packaged is formed as a tray having multiple chambers, each of which contains pre-loaded capsules and a quantity of preservative liquid whereby the respective chambers are sealed by an overlying cover sheet.

11 Claims, 2 Drawing Sheets

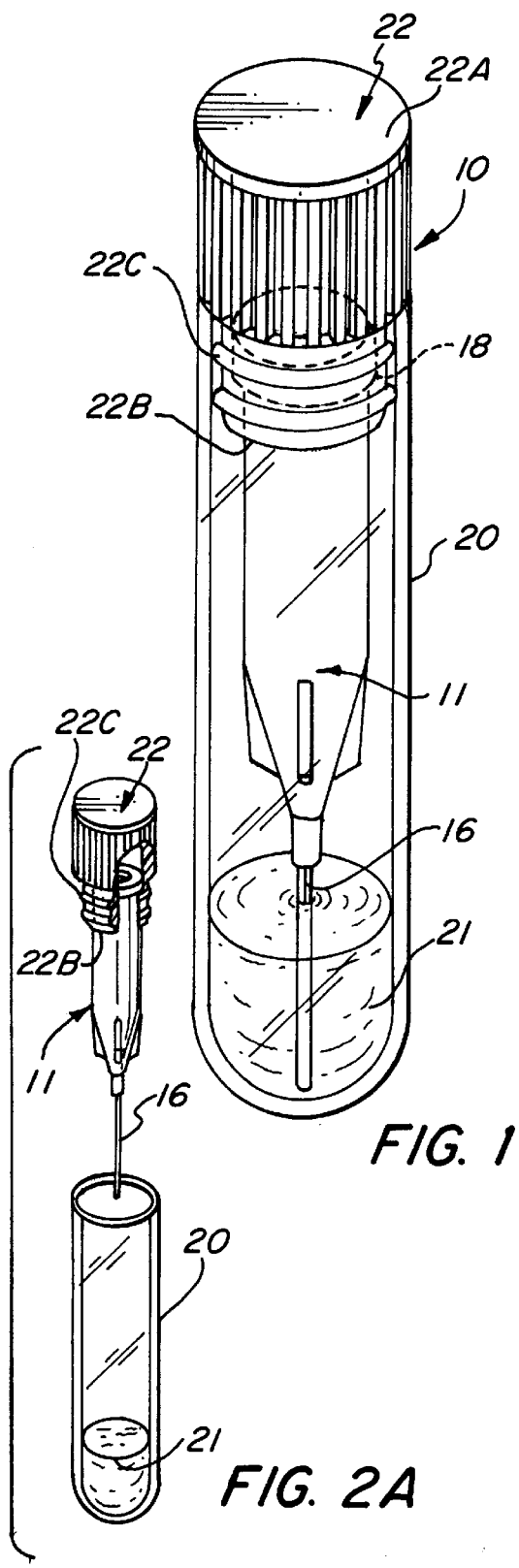
FIG. 1
FIG. 2A
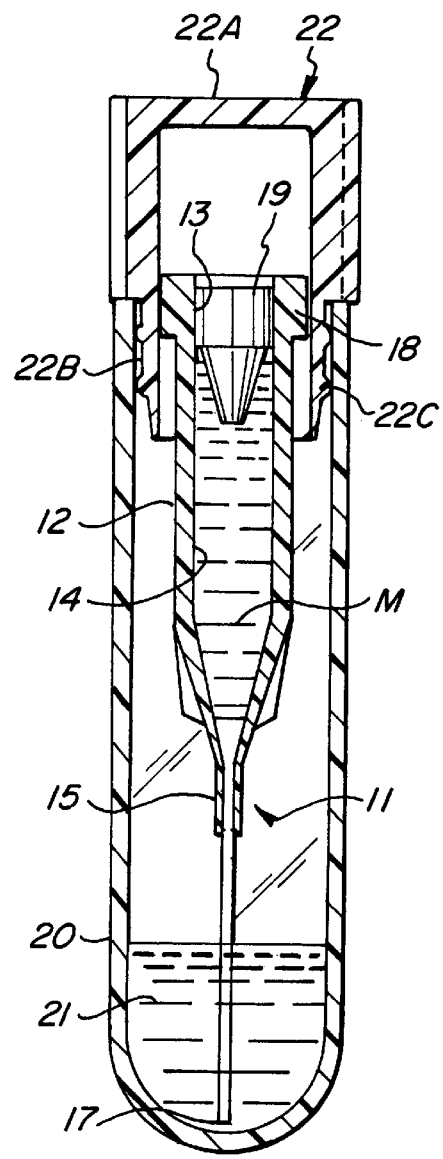
FIG. 2

5,819,921

CALCIUM HYDROXIDE PACKAGE AND METHOD OF FORMING SAME

FIELD OF THE INVENTION

This invention relates generally to a package for calcium hydroxide formulation, and more specifically to a unit or single dose package of calcium hydroxide formulation to prohibit long term changes in consistency due to dehydration or chemical reactions in the presence of any carbon dioxide, and method of making the same.

PROBLEM AND PRIOR ART

In dentistry, calcium hydroxide formulated paste is frequently used as a temporary treatment material to pack a root canal of a tooth during a root canal procedure. Heretofore, such calcium hydroxide paste was packaged in relatively large (five cc) syringes or in an anesthetic type glass cartridge. When packaged in a large bulk syringe, a dentist would first extrude therefrom a desired amount of the calcium hydroxide paste for a given procedure onto a pad or dispensed from the bulk syringe using a disposable canula. Calcium hydroxide so packaged can lead to cross contamination, since it is impossible for a dentist to sterilize a bulk syringe with the remaining material inside. The dentist would then pack the extruded amount of calcium hydroxide paste into the root canal of a tooth. It has been noted in the packaging of such calcium hydroxide paste in a bulk syringe type package that there is also the tendency for the calcium hydroxide paste to harden or solidify over time because of dehydration and/or by reaction with any carbon dioxide which may be present, thereby rendering such paste unfit for its intended use. As a result, much of the paste packaged in such bulk type package syringes often would solidify before it was used, thereby resulting in substantial waste. In an effort to alleviate this solidifying problem, dentists were instructed to moisten the tip end of the bulk syringe before recapping the tip end between use thereof. However, such instructions provided only marginal success depending upon the integrity of the sealing cap and end piston. Also, dentists and/or the dental assistants frequently would neglect and/or not follow such manufacturer's instructions.

When packaged in anesthetic type glass cartridge with attached needle, the sterility of the calcium hydroxide was compromised, as the same cartridge was used on multiple patients that required the attachment of a new needle for each patient.

SUMMARY OF THE INVENTION

An object of this invention is to provide a calcium hydroxide package which includes a dispensing capsule having a needle discharge, which is preloaded with a unit dose of calcium hydroxide, and in which the discharge end of the needle nozzle and the piston end of the capsule is sealed in a vial containing fluid to prohibit any solidification of the calcium hydroxide.

Another object is to provide a capsule preloaded with a unit dose of calcium hydroxide and from which calcium hydroxide can be directly delivered to a prepared tooth by a syringing technique wherein the capsule is sealed within an enclosure containing preservative fluid until readied for use.

Another object is to provide a calcium hydroxide package that includes a dispensing capsule preloaded with a predetermined amount of calcium hydroxide in a sealed vial having a closure frictionally receiving an end portion of the capsule so that as the closure is removed from the vial, the capsule is withdrawn from the vial.

Another object of this invention is to provide a capsule that is preloaded with a predetermined amount of calcium hydroxide having a uniform consistency to provide a smooth, predictable dispensing flow during extrusion by utilizing only a reasonable amount of syringing pressure or force.

Another object is to provide a multi-package containing a plurality of preloaded capsules wherein the respective capsules are disposed in an individual sealed chamber that contains a quantity of distilled water saturated with calcium hydroxide.

The foregoing objects and other features of the invention are attained by a capsule having a needle discharge nozzle connected thereto, and which capsule is preloaded with a predetermined amount of calcium hydroxide and closed at the other end by an end plug or piston. The capsule so loaded is then placed in a vial or chamber containing a preservative fluid, e.g. distilled water or distilled water saturated with dissolved calcium hydroxide, whereby both the discharge end of the needle or nozzle and the piston end of the capsule is wholly disposed within the vial or chamber with the preservative fluid. The vial or chamber is then sealed and remains sealed until ready for use. The sealed vial or chamber and preloaded capsule therein, together with the fluid, is then sterilized, e.g. by a gamma sterilization process, to render the entire package sterile. In another form of the invention, a plurality of capsules, each preloaded with calcium hydroxide are packaged in a multi-package comprising a vacuum formed pack or tray having a plurality of chambers, each chamber being sized to receive one preloaded capsule. A quantity of distilled water, which may be saturated with dissolved calcium hydroxide, is disposed in each chamber. The multiple chambers are then sealed by a cover or barrier of a moisture proof film or sheet. The multi-pack so formed is then sterilized.

IN THE DRAWINGS

FIG. 1 is a perspective view of a sterile calcium hydroxide package embodying the invention.

FIG. 2 is a sectional side view of FIG. 1.

FIG. 2A is a detail exploded view of FIG. 1.

DETAILED DESCRIPTION

Figure 3:
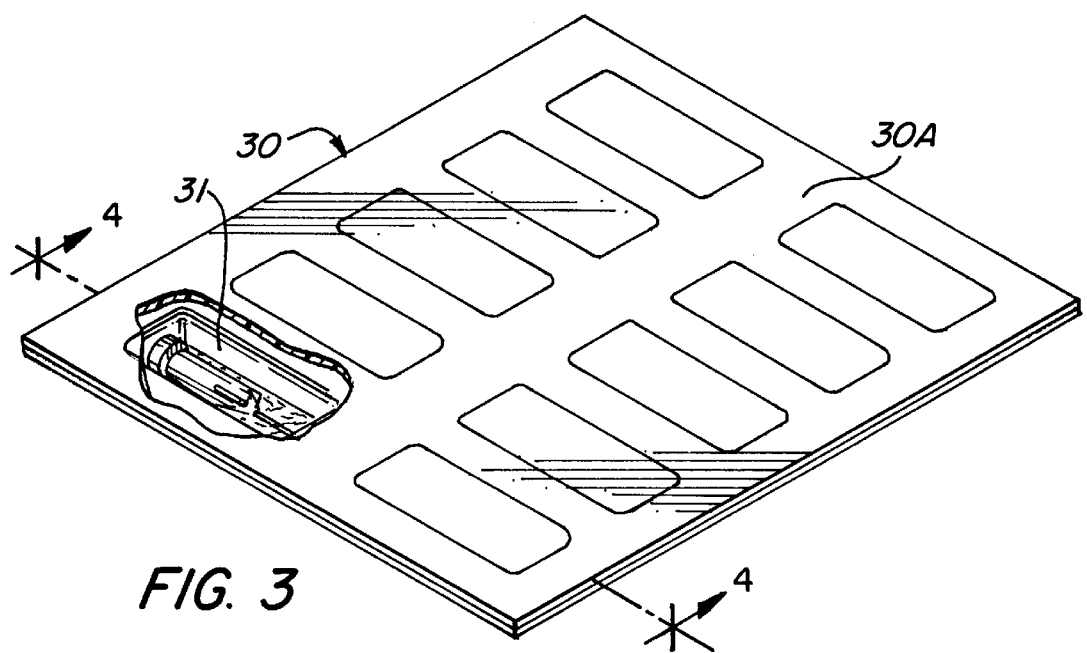
FIG. 3 is a perspective view of a multi-pack container embodying the invention and having parts broken away.

Referring to the drawings, there is shown in FIG. 1 a package 10 for storing and dispensing a calcium hydroxide formula and the like for use as a treatment in a dental root canal procedure. As shown, the package 10 includes a capsule 11 having a body portion 12 which is open at one end 13 to define a reservoir 14 for receiving a single or unit dose of a predetermined amount of a calcium hydroxide formulation "M". The other end 15 of the capsule has connected thereto a needle cannula 16 to define a nozzle which is open at its discharge end to form a discharge orifice 17. Preferably, the needle cannula is formed with a gauge ranging between 18 to 30. A laterally outwardly extending flange 18 circumscribes the open end 13 of the capsule 11. A piston or end plug 19 is fitted into the open end 13 to provide a closure for confining the calcium hydroxide paste "M" within the reservoir 14. The capsule 11, as described, is of a type disclosed in U.S. Pat. No. 5,336,088 granted Aug.

9, 1994 and which disclosure is incorporated herein by reference. It will be understood that the material "M" within the capsule 11 may be directly delivered to the tooth by placing the capsule 11 in a syringe of the type disclosed in said U.S. Pat. No. 5,336,088 or any of the several types of dental extruders or syringes manufactured and patented by Centrix, Inc. The formulation of the calcium hydroxide is such that its particular mesh size be smaller than the bore of the needle cannula.

In accordance with this invention, a capsule 11, so loaded as herein described, is placed in a vial 20 as shown in FIG. 1. Disposed within the vial 20 is a quantity of liquid 21, e.g. distilled water or distilled water saturated with calcium hydroxide. As illustrated in FIG. 1, the open end or orifice 17 of the needle cannula 16 is maintained submerged below the level of the liquid. This is attained by sizing the vial 20 to receive a loaded capsule 11 so as to maintain the capsule 11 in the vertical position with the open end 17 of the cannula needle disposed below the level of the liquid. The vial 20 is then sealed by an end closure or sealing cap 22. However, laying the vial on its side during storage is just as effective in maintaining the shelf life of the calcium hydroxide within the capsule.

As shown in FIG. 1, the sealing cap 22 is substantially cylindrical in configuration, closed by a top end wall 22A and having the opposite end 22B sized so as to be frictionally received within the open end of the vial 20. The end 22B arranged to be inserted into the vial 20 is provided with one or more circumscribing ribs 22C to form a fluid tight seal when the sealing cap 22 is fitted into the vial 20.

The inner cylindrical portion 22B of the sealing cap 22 is sized so as to frictionally receive the flanged end 18 of the capsule 12. The arrangement is such that when the sealing cap 22 is removed from the vial as shown in FIG. 2A, the capsule 11 is withdrawn from the vial 20 as the sealing cap 22 is removed due to the frictional interconnection between the sealing cap 22 and the flanged end 18 of the capsule 11.

The fluid, as described, prevents any drying out and/or chemical degradation of the calcium hydroxide formulation within the capsule during storage to preserve the freshness of the formulation while substantially extending the useful life or shelf life of the formulation. The distilled water 21, when used as the fluid, acts as a barrier by precipitating any calcium carbonate which may be formed by any ambient $CO_2$ in the air entrapped within the vial.

The capsule 11, preloaded with a predetermined amount of calcium hydroxide M and sealed within the vial 20 as herein described, may then be subjected to a sterilization process, e.g. gamma sterilization, to provide for a final sterile calcium hydroxide paste package.

In accordance with this invention, the calcium hydroxide preloaded within the capsule 11 is formulated to have uniform consistency to insure a smooth, predictable dispensing flow with a reasonable syringe force. This can be achieved by controlling the formulation, storage and handling of the bulk calcium hydroxide composition and including the screening of the composition to exclude any particle sizes larger than one half of the needle orifice diameter.

If desired, the preservative fluid 21 may contain calcium hydroxide in suspension to function as a barrier to prevent the presence of any carbon dioxide from reacting with the calcium hydroxide within the capsule 11 which, if allowed to occur, would then cause hardening or solidification in the form of calcium carbonate in the needle tip or about the piston 19. Any carbon dioxide that is either trapped within the head space of the vial during assembly or that may migrate over time slowly into the vial, will react with the suspended calcium hydroxide in the preservative fluid to form a harmless precipitation within the vial. Accordingly, hardening of the calcium hydroxide within the capsule 11 is prevented, regardless of the location or position of the volume of preservative fluid 21 within the vial. This result is achieved whether the vial is stored on its side or in a vertical position as shown in FIGS. 1 and 2.

Figure 4:
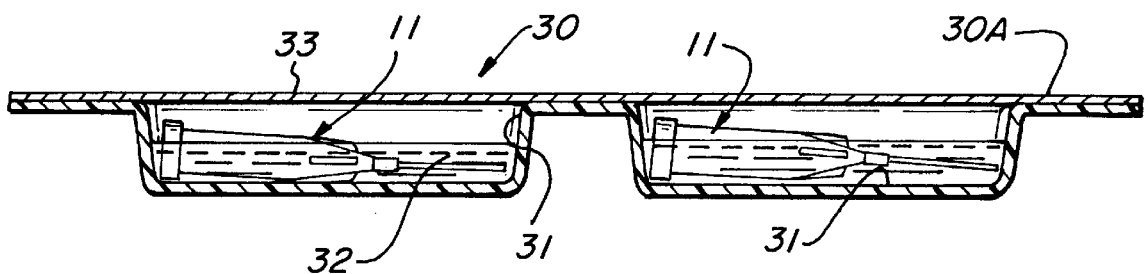
FIG. 4 is a section view taken on line 4—4 on FIG. 3.

FIGS. 3 and 4 illustrate a further embodiment of the invention. In this form of the invention, the package comprises a tray 30 which is preferably formed of a thin sheet of a suitable liquid impervious plastic material 30A which can be readily vacuum formed with a plurality of independent chambers or wells 31. In the illustrated embodiment, two rows of six wells or chambers 31 are formed at spaced apart intervals as shown. It will be noted that the open end of each chamber or well 31 is formed in the plane of the molded sheet 30A. The arrangement is such that a capsule 11, as hereinbefore described and preloaded with a predetermined amount of calcium hydroxide, is placed in each chamber or well 31. A quantity of a preservative fluid 32 is placed within each chamber 31 so as to prohibit any dehydration and/or chemical decomposition of the calcium hydroxide as hereinbefore described.

Sealing the capsule 11 and preservative fluid 32 in each of the respective chambers or wells 31 is achieved by a cover sheet 33, which is co-extensive to the area of tray 30. It will be understood that the cover sheet 33 may be formed of a suitable liquid impervious plastic film or sheet which may be adhesively secured or heat sealed to the upper surface of the tray 30 to form a liquid tight seal about each of the respective chambers or wells 31.

In this form of the invention, there is provided a multi-package wherein the individual capsules 11 can be readily removed as needed merely by perforating that portion of the covering sheet extending over the chamber of the capsule selected without breaking the sealing integrity of any other chambers or wells 31.

It will be understood that in all other respects, the multi-package of FIGS. 3 and 4 will function and operate in a manner as hereinbefore described with respect to FIGS. 1 and 2, and sterilized as hereinbefore described.

While the present invention has been described with respect to more than one embodiment, modifications and variations may be made without departing from the spirit or scope of the invention.

What is claimed is:

1. A package for storing, distributing and dispensing a dental material for a tooth restoration procedure comprising:

an outer enclosure defining a compartment, said enclosure having an opened end, a capsule disposed within said enclosure, said capsule having a body portion defining a reservoir, said body portion being opened at one end, and a cannula defining a nozzle connected to the other end of said body portion, said cannula having a bore extending therethrough, one end of said cannula being in communication with said reservoir and the other end of said cannula defining an open discharge end, a predetermined amount of calcium hydroxide material disposed in said reservoir, an end plug fitted to the open end of said body portion for sealing said calcium hydroxide within said reservoir, a supply of liquid defining a liquid level within said outer enclosure, said capsule being disposed in said outer enclosure so that said open discharge end of said cannula extends below the liquid level in said outer enclosure to form a liquid seal for the open discharge end of said cannula, and an end closure for sealing said capsule and liquid within said outer enclosure.

2. The package as defined in claim 1 wherein said supply of liquid comprises distilled water.

3. The package as defined in claim 1 wherein said supply of liquid includes calcium hydroxide suspended therein.

4. A package for storing, distributing and dispensing a dental material comprising:

a vial having an open end portion;

a capsule disposed within said vial, said capsule having a body defining a reservoir which is opened at one end;

a needle cannula connected to the other end of the capsule body in communication with said reservoir;

said cannula having an open discharge end;

a predetermined amount of a calcium hydroxide formulation disposed in said reservoir, an end plug for sealing said open end of said reservoir;

a liquid supply defining a liquid level disposed in said vial; and a closure for sealing said capsule and liquid supply within said vial whereby the discharge end of said cannula is disposed below the level of the liquid supply in said vial.

5. The package as defined in claim 4 wherein said capsule includes a laterally extending flange circumscribing said open end of said body.

6. A calcium hydroxide paste package as defined in claim 5 wherein said closure includes an inner cylindrical portion adapted to be received within the open end of the vial to form a fluid tight seal;

and said inner cylindrical portion frictionally engaging the said flange in the sealing position of said closure, whereby said capsule is withdrawn from said vial as said closure is removed therefrom.

7. A package as defined in claim 6 and including a rib circumscribing said inner cylindrical portion of said closure to form a fluid tight seal.

8. A method of packaging a temporary treatment material adapted for use in a root canal procedure comprising the steps of:

forming a capsule having a nozzle defining a discharge orifice;

filling said capsule with a predetermined amount of calcium hydroxide dental treatment material;

sealing the end of said capsule with a displaceable plug;

placing said filled capsule into an enclosure;

disposing an amount of preservative liquid in said enclosure, and sealing said enclosure to confine said capsule and liquid within said chamber, whereby said discharge nozzle is disposed below the level of said liquid to prohibit dehydration and decomposition of said calcium hydroxide treatment material.

9. The method as defined in claim 8 and including the step of sterilizing said enclosure with said capsule and liquid contained therein.

10. A package for storing a dental material comprising:

a capsule;

a cannula extending from said capsule;

a calcium hydroxide material placed within said capsule;

a container having an open end, said capsule placed within said container;

a preserving liquid placed within said container; and a seal covering the open end of said container, whereby said calcium hydroxide is prevented from solidifying while in said container.

11. A package as in claim 10 wherein:

said preserving liquid comprises distilled water saturated with dissolved calcium hydroxide.

\* \* \* \* \*